United States Patent [19]

Geho

[11] Patent Number: 4,761,287

[45] Date of Patent: Aug. 2, 1988

[54] DIABETES CONTROL BY SEROTONIN

[75] Inventor: Walter B. Geho, Wooster, Ohio

[73] Assignee: Technology Unlimited, Inc., Wooster, Ohio

[21] Appl. No.: 849,849

[22] Filed: Apr. 9, 1986

Related U.S. Application Data

[63] Continuation-in-part of Ser. No. 606,714, May 3, 1984, Pat. No. 4,603,044.

[51] Int. Cl.$^4$ ............... A61K 37/22; A61K 9/42; B01J 13/02
[52] U.S. Cl. .................. 424/450; 428/402.2; 436/829; 514/866; 514/893
[58] Field of Search .............. 428/402.2; 424/450; 436/829; 514/866, 893

[56] References Cited

U.S. PATENT DOCUMENTS

| | | | |
|---|---|---|---|
| 4,377,567 | 3/1983 | Geho | 424/450 X |
| 4,603,044 | 7/1986 | Geho et al. | 424/450 X |

Primary Examiner—Richard D. Lovering
Attorney, Agent, or Firm—Frijouf, Rust & Pyle

[57] ABSTRACT

A discovery that insulin alone does not fully control liver function of glucose uptake, release, and synthesize. A second hormone, serotonin, is released in the portal vein as a function of glucose presence in the gut and portal vein. In the absence of the portal serotonin, the liver will not take up and store glucose, and will, in fact, synthesize more glucose.

Adult onset diabetics generally do not have a lack of natural insulin. Whenever a serotonin deficiency is the lacking control factor, this hormone is supplied by a hepatocyte diected vesicle (HDV) containing serotonin timed to reach the liver with the supply of glucose from a meal.

5 Claims, 3 Drawing Sheets

DIABETES CONTROL BY SEROTONIN

RELATED SUBJECT MATTER

This application is a continuation-in-part of U.S. Ser. No. 606,714, now U.S. Pat. No. 4,603,044 filed May 3, 1984 and issued July 29, 1986.

BACKGROUND OF THE INVENTION

1. Field of the Invention

This invention is a discovery that Serotonin is a cofactor in liver glucose management.

2. Description of the Prior Art

Serotonin is a known hormone, 5-hydroxytryptamine (5HT), present in platelets, gastrointestinal mucosa, mast cells, and in carcinoid tumors. Serotonin is a potent vasoconstrictor. It is thought to be involved in neural mechanisms important in sleep and sensory perception. (Taber's Cyclopedic Medical Dictionary, 14 Ed.)

SUMMARY OF THE INVENTION

This invention resides primarily in the discovery that Serotonin is a second required hormone in glucose management by the liver of a warm blooded animal.

With that discovery in place, it is then the function of this invention to successfully and properly deliver this required hormone to the liver by means of a hepatocyte directed vesicle (HDV).

DETAILED DESCRIPTION

Figure 1:
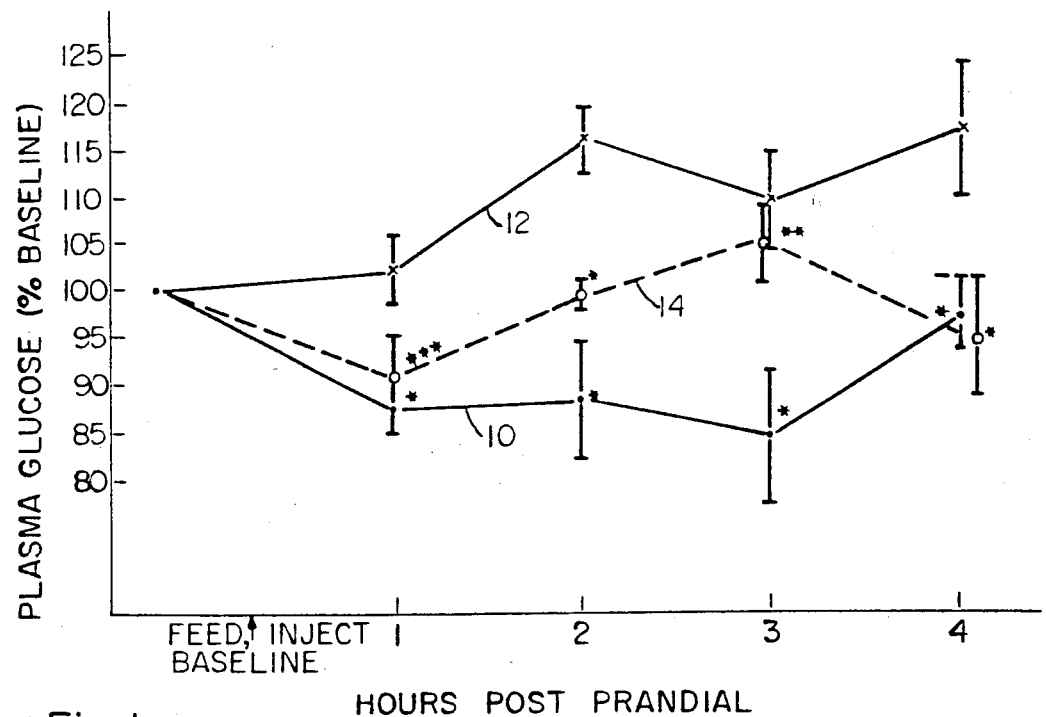
FIG. 1 is a comparison chart of testing in which normal dogs are charted, followed by surgical denervation, and finally resteration by the procedures of these invention.
Figure 2:
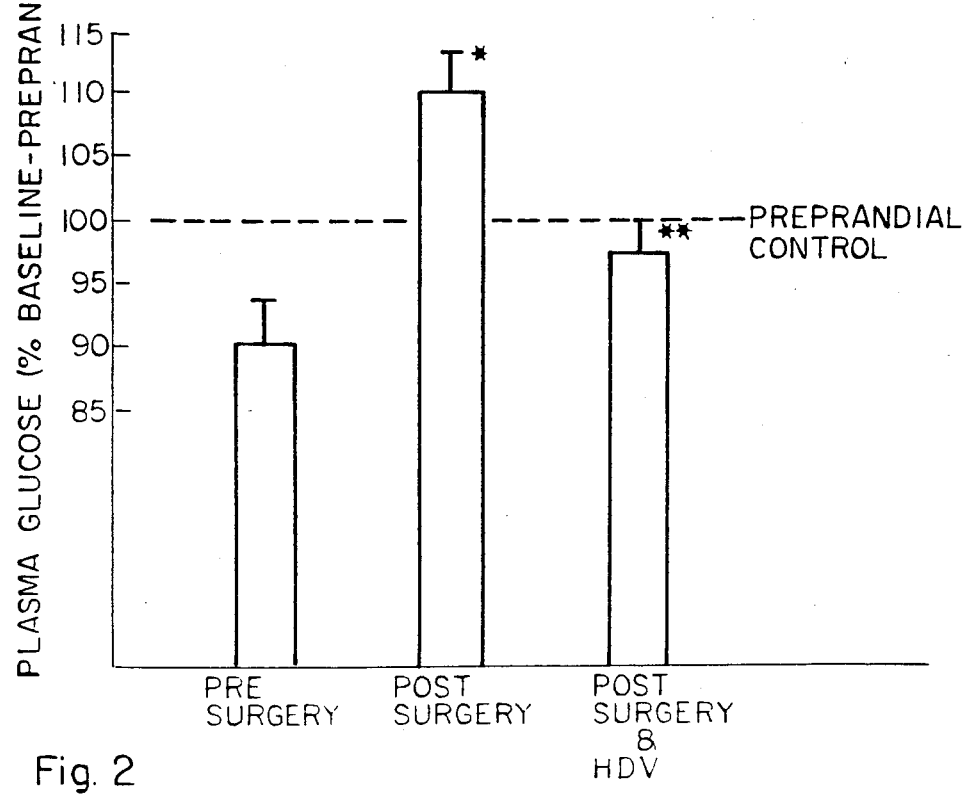
FIG. 2 is a summary of the data in bar form.
Figure 3:
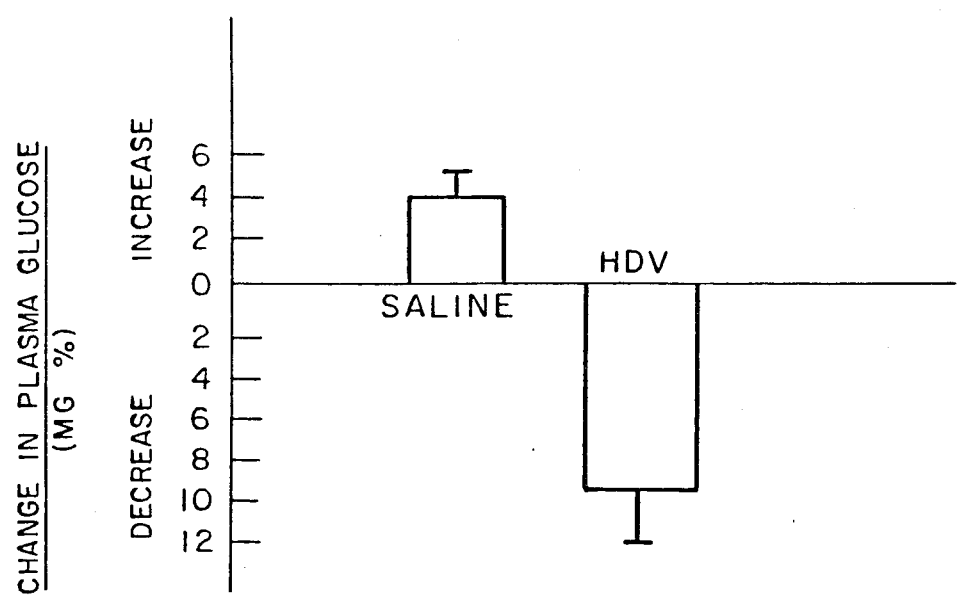
FIG. 3 summarizes the results of dog denervated and compared on one day saline solution and the second day with procedures of the present invention.

The liver is the human body's largest gland and, as such, receives a massive blood supply through both the portal vein and hepatic artery. Metabolically, the liver is the most complex organ in the human body and, among other multiple functions, it metabolized/distributes drugs which are introduced into the organism. The liver is also a target organ for pharmacologically-active agents produced within the body. Accordingly, an improved means for preferentially delivering drugs to the liver provides a means for allowing the drug to be handled by the body in a more natural fashion, thereby improving drug therapy.

The means whereby the liver handles insulin illustrates the activity of this important target organ.

Insulin is a hormone which affects the metabolism of the animal as a whole. The most dramatic effect of this hormone is its ability to reduce the concentration of glucose in blood plasma. Ingested carbohydrate meals are normally digested to glucose in the gut and then absorbed in the portal circulation. The pancreas responds to carbohydrate in the gut with a release of insulin into the portal circulation. The portal vein carries the absorbed glucose and the released insulin to the liver. At the liver the insulin regulates the metabolism of glucose by the hepatocytes. By an unknown mechanism the liver retains most of the insulin but releases some to facilitate glucose utilization by muscle and adipose tissue. Reduction in blood glucose is due to the insulin effect on both liver and peripheral tissues. Thus, while the pancreas is the source of insulin within the organism, the liver is the key to its normal utilization.

It is now known, according to this invention, that Serotonin is another key.

The liver is a difficult organ to reach with exogenously administered drugs, and the HDV presents a unique therapeutic advance, making it possible to deliver drugs, hormones, biologicals and diagnostic materials in a more efficient, safer way than those means currently available. The reason for the "therapeutic unavailability" of the liver to conventional therapies is that the liver is anatomically situated in such a way that it is isolated from the rest of the body with respect to its blood circulation. The majority of the liver's blood comes to it by way of the portal circulatory system which is a highly localized, low-pressured, venous system designed to carry absorbed nutrients (product of digestion) from the intestines to the liver for metabolism. The arterial blood supply takes care of the rest of the body before a small portion of it reaches the liver via the portal system.

According to this invention, it has been discovered that the liver storage of glucose eaten during a meal requires not only the hormone insulin, but also that a co-factor is required for proper liver function. That co-factor is serotonin. Serotonin is a chemical, 5-hydroxytryptamine (5-HT), present in platelets, gastrointestinal mucosa, mast cells, and in carciniod tumors. Serotonin is a potent vasoconstrictor (Taber's Cyclopedic Medical Dictionary, 14th Edition). This inventor has established that serotonin is supplied to the portal vein leading to the liver while food is being absorbed by the intestines and is controlled by the central nervous system. Thus, it was discovered that by severing the vagus nerve the serotonin in the portal vein can be essentially eliminated. When this is done, it is now established, the liver no longer will convert the nutrient glucose to glycogen and store the glycogen. Rather, the liver will allow all of the glucose to proceed into the peripheral system, thereby producing excess sugar in the blood and providing the symptoms of diabetes. Although there may be sufficient insulin available at all times at the liver, a deficiency of serotonin will result in an excess of glucose in the blood.

By providing a serotonin load in this hepatocyte delivery vesicle and targeting the vesicle to the hepatobiliary receptors of the liver, and observing the return to normal liver function, this inventor has clearly established the discovery of the co-factor control function of Serotonin.

Hence, in a dog model having a normal insulin production by the pancreas glands, it is a superior test of the function of Serotonin to denervate the glands in the portal vein producing serotonin, and after establishing diabetes symptoms of excess blood glucose, to direct serotonin (5HT) to the liver. Re-establishment of normal liver glucose control then proves the function of serotonin in glucose control.

In a first study testing the serotonin function, a chronic dog model was selected which mimics the early stages of adult onset diabetes mellitus, now referred to as diabetes mellitus Type II. In this model, the diabetes was induced by selective denervation. The normal healthy dogs prior to denervation respond to a standard meal (one-third carbohydrate) by having slightly lowered levels of peripheral blood glucose. Following denervation, the dogs maintain normal fasting blood glucose values, but their peripheral blood glucose levels rise significantly after a standardized meal, thus responding in a similar manner to adult onset diabetes.

This particular model was selected for this study because it enabled the evaluation of the role of serotonin in alert, unanesthesized animals.

This study was divided into three phases, studying the blood glucose response of the animals while in the (1) normal state; (2) diabetic-like state; and (3) successful treatment of the diabetic-like state with subcutaneously administered HDV containing serotonin.

The experimental plan required four normal, healthy mongrel dogs. This first phase of the study was to determine the blood glucose response of these four dogs to a standardized glucose meal, comparable to the oral glucose tolerance test in people. The graph of FIG. 1 is a comparison chart for in vivo testing.

The data for this normal phase are shown in the graph as the line indicated by reference number 10. The data are expressed as a percentage of the fasting blood glucose value taken prior to feeding. Since four dogs were used, the average of means value for the data is plotted. The data are statistically analyzed, and the variation in the data is shown by the small vertical bars above and below the data points. These bars are the standard error of the mean (SEM).

Following the acquisition of the data described above, the dogs were surgically denervated to induce the diabetic-like state and allowed a week to recover. At this time the study is again repeated, and the data are shown as the line indicated by the reference number 12, along with the error bars (SEM). It is clearly seen from the data that the animals' responses were different following the denervation. The asterisks (*) at the 1,2,3 and 4 hour data points along the line 10 indicate that by statistical analysis of the data by the conventional student's test, the blood glucose response of the dogs following surgery is statistically different from the response to the dogs prior to surgery. The level of significance is less than 5%. This means that there is less than a 5% chance that the difference observed would have happened randomly.

The third phase of the study was to repeat the standardized meal in the diabetic-like dogs, but with the dogs injected subcutaneously with 1.0 ml of HDV-containing serotonin. The total dose of serotonin in the HDV was 150 ug serotonin, and it was administered one hour prior to eating and immediately after taking the baseline blood glucose sample. The response of the HDV-serotonin-treated denervated dogs is shown in line 14. The abnormal elevation of the blood glucose has been lowered.

The data from these studies are summarized in the bar graph of FIG. 2.

The first bar shows that the average value for the blood glucose (hours 1–4) for the dogs prior to surgery decreased about 10% after a meal compared to their blood glucose value taken prior to eating. In the second bar, the mean blood glucose response (hours 1–4) was increased after a meal, and the asterisk indicates that it was statistically significant ($p<0.01$, student's test). The denervation had caused an elevation in blood glucose following a meal, thus inducing a diabetes-like state. The third bar shows the effect of the HDV-serotonin treatment. The HDV serotonin significantly decreased the elevation of the blood glucose following a meal.

It is most important to know that in studies by the inventor it has been established that serotonin administered at this dose (150 ug) is not effective either intravenously or subcutaneously in inducing the effect seen with the HDV-serotonin in these studies.

The conclusions from these data are:

1. Denervation produced a diabetic-like state.

2. The effects of denervation could be corrected with very low doses of HDV containing 5-HT.

A second study tested the hypoglycemic (blood glucose-lowering ability) effectiveness of HDV containing 5-HT in fasting (non-fed) dogs. The graph of FIG. 3 summarizes the results. Four dogs (denervated as in the first study) were used in the study on two different days. The first day tested the effect of saline and the second day, the effect of HDV (with 5-HT) on fasting plasma glucose levels. The protocol required that a baseline plasma glucose be obtained and followed by a 1.0 ml subcutaneous injection of saline (day 1) or HDV/5-HT (day 2). One hour later a second blood sample was obtained for a post-treatment plasma glucose. The post-treatment glucose was compared to the baseline plasma glucose values. The saline treatment (control) experiment resulted in an increased plasma glucose compared to its baseline values. However, the HDV/5-HT treatment resulted in a statistically significant reduction in fasting plasma glucose.

The conclusions based on this data are:

1. Control saline injections in fasting dogs produced a slight (statistically insignificant) increase in the fasting plasma glucose.

2. HDV/5-HT injections produced a statistically significant reduction of the fasting plasma glucose.

The second conclusion, namely the administration of the HDV-5HT and the resultant reduction in fasting plasma glucose is quite significant. Bearing in mind that the purpose for the foregoing test is to establish conclusively that the serotonin, delivered by the proven HDV system, together with the unimpaired natural insulin supply, is a joint factor in proper liver function of a warm blooded animal. Therefore, this invention, having first established the function in serotonin in programming the liver to uptake glucose, and then administering the serotonin in the HDV with the resultant reduction in glucose, establishes beyond any reasonable doubt that the HDV has been taken into the liver and has caused the function expected of Serotonin of ceasing glucose output and beginning glucose uptake.

SUPPLEMENTAL EXPERIMENT

HDV Serotonin: Intraduodenal (Oral)

HDV serotinin prepaired as in the teaching of U.S. Pat. No. 4,603,044.

Route of administration: Intraduodenal injection (oral)

The purpose of this experiment was to demonstrate the efficacy of HDV Serotonin, constructed with the above materials, in a selectively denervated dog that was not insulin-deficient, but in a diabetic-like state. In this model, the response of the HDV Serotonin was the conversion of hepatic glucose output to uptake. This conversion was determined by measuring the glucose levels (Beckman Glucose Analyzer) in simultaneously obtained blood samples from the portal and hepatic veins. Sampling was by means of sampling catheters acutely placed under general anesthesia.

The state of hepatic glucose output occurs when the level of glucose (mg %) in the hepatic vein exceeds that of the portal vein. Hepatic glucose uptake is the reverse situation.

Figure 4:
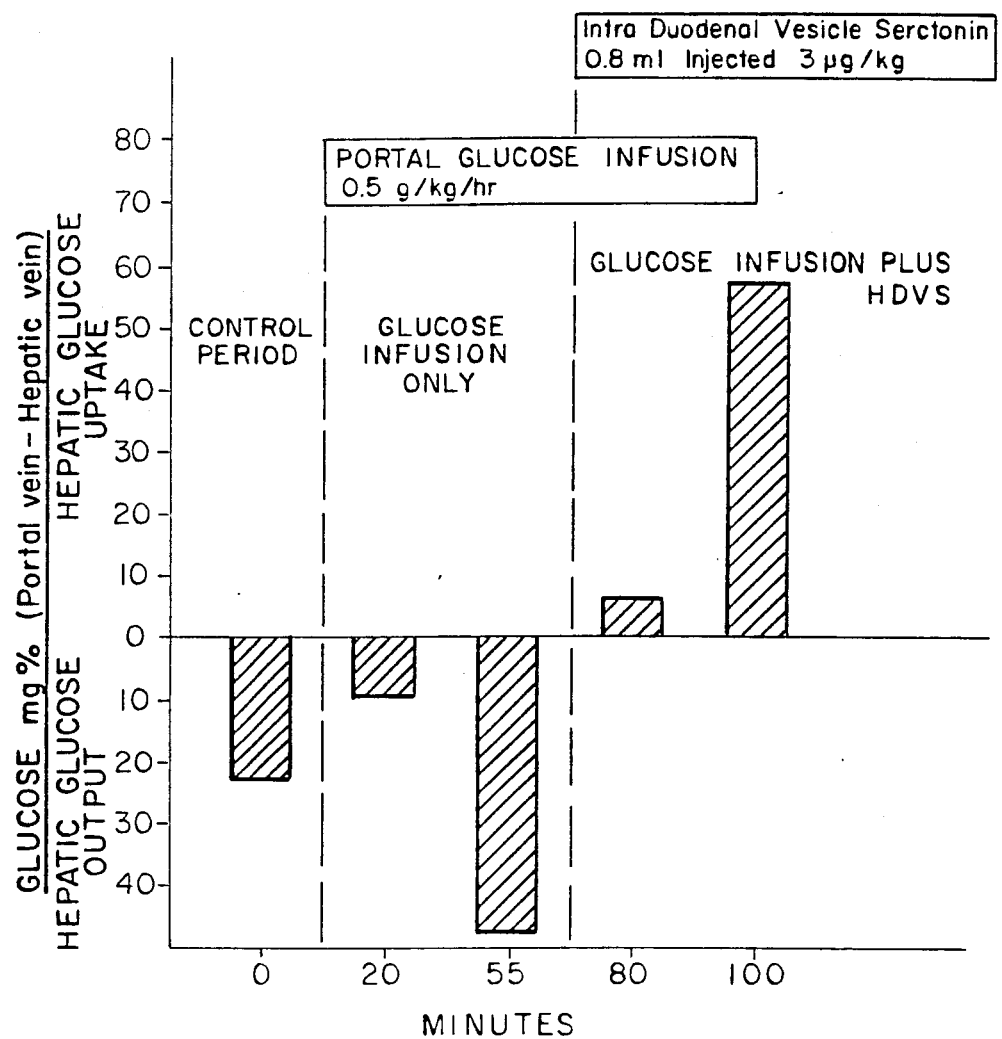
FIG. 4 is a graph demonstrated the efficiency of serotonin delivered by hepatocyte directed vesicle and selectably denervated dogs that were not insuline deficient, but in a diabetic-like state.

Data for the experiment are found in FIG. 4. At "0" minutes, during the control period, the animal is in a state of hepatic glucose output. Because of the selective denervation, the animal stays in output (at 20 and 55 minutes), even though glucose is being infused at a rate of 0.5 g/kg body weight/hour via a mesenteric vein.

The HDV Serotonin is injected into the duodenum (0.8 ml containing 3 ug serotonin/kg) after 60 minutes. At 80 and 100 minutes the HDV Serotonin has converted the hepatic glucose output to uptake.

The conclusions are: (1) HDV Serotonin can cross from the lumen of the intestine into the blood and deliver HDV Serotonin to the hepatocyte where the serotonin is released and can carry out its pharmacologic function, and (2) HDV Serotonin is superpotent. The single intraduodenal injection of serotonin (3 ug/kg) produced a pharmacolgic effect that would have required an intraportal infusion of 10–30 ug/kg body weight/minute for thirty minutes (total infused dose of serotonin per kg body weight). The intrduodenal dose was 1/300th of the necessary intraportal dose of free hormone.

What is claimed is:

1. The method of programming the liver of a warm blooded animal to take up glucose from the portal vein whenever there is a sufficient insulin supply but abnormal elevation of blood glucose, comprising administering serotonin to said animal in an hepatocyte targeted vesicle prior to food ingestion.

2. The method of treatment of hyperglycemia in a warm blooded animal suffering from excess blood glucose levels and the presence of functional insulin levels at the liver, said method comprising the step of administering to said animal a therapeutically effective dose of serotonin contained in a liposome having a target substituent selected from the class of those chemicals which are classed biologically as having a high affinity for the hepatocytes of the liver.

3. In the method of claim 1 or 2, said administration being accomplished one hour prior to food ingestion.

4. In the method of claim 1 or 2, the administration being done by subcutaneous injection.

5. In the method of claim 1 or 2, the administration being orally to the duodenum of the animal.

* * * * *